US010597620B2

(12) United States Patent
Chien et al.

(10) Patent No.: US 10,597,620 B2
(45) Date of Patent: Mar. 24, 2020

(54) TASTE MODIFIERS COMPRISING A CHLOROGENIC ACID

(71) Applicant: GIVAUDAN SA, Vernier (CH)

(72) Inventors: Minjien Chien, West Chester, OH (US); Alex Häusler, Hedingen (CH); Hans Van Leersum, Morrow, OH (US)

(73) Assignee: Givaudan SA, Vernier (CH)

( * ) Notice: Subject to any disclaimer, the term of this patent is extended or adjusted under 35 U.S.C. 154(b) by 0 days.

(21) Appl. No.: 15/662,950

(22) Filed: Jul. 28, 2017

(65) Prior Publication Data

US 2017/0327776 A1  Nov. 16, 2017

Related U.S. Application Data

(60) Continuation of application No. 13/436,254, filed on Mar. 30, 2012, now abandoned, which is a division of application No. 10/480,372, filed as application No. PCT/CH02/00315 on Jun. 12, 2002, now Pat. No. 8,197,875, which is a continuation of application No. 09/880,420, filed on Jun. 13, 2001, now abandoned.

(51) Int. Cl.
| | | |
|---|---|---|
| *A23L 27/00* | (2016.01) | |
| *C12G 3/04* | (2019.01) | |
| *A23C 9/13* | (2006.01) | |
| *A23C 11/10* | (2006.01) | |
| *A23L 2/56* | (2006.01) | |
| *A23L 2/60* | (2006.01) | |
| *A61K 36/74* | (2006.01) | |
| *A23L 27/20* | (2016.01) | |
| *A23L 27/30* | (2016.01) | |

(52) U.S. Cl.
CPC .............. *C12G 3/04* (2013.01); *A23C 9/1307* (2013.01); *A23C 11/103* (2013.01); *A23L 2/56* (2013.01); *A23L 2/60* (2013.01); *A23L 27/204* (2016.08); *A23L 27/2026* (2016.08); *A23L 27/30* (2016.08); *A23L 27/84* (2016.08); *A61K 36/74* (2013.01)

(58) Field of Classification Search
CPC ....... C12G 3/04; A23L 27/30; A23L 27/2026; A23L 27/204; A23L 27/84; A23L 2/56; A23L 2/60; A23C 9/1307; A23C 11/103; A61K 36/74
USPC ....... 416/321, 532, 534, 536, 538, 548, 650, 416/654
See application file for complete search history.

(56) References Cited

U.S. PATENT DOCUMENTS

| | | |
|---|---|---|
| 3,916,028 A | 10/1975 | Lee et al. |
| 4,495,170 A | 1/1985 | Beyts et al. |
| 4,710,583 A | 12/1987 | Chmurny et al. |
| 4,872,987 A | 10/1989 | Kopsch et al. |
| 5,788,971 A | 8/1998 | Togasaki |
| 5,888,549 A | 3/1999 | Buchholz et al. |
| 6,426,112 B1 | 7/2002 | Boatright |
| 6,475,544 B1 | 11/2002 | Hiramoto et al. |

FOREIGN PATENT DOCUMENTS

| | | |
|---|---|---|
| CN | 1085073 | 4/1994 |
| EP | 1186297 A2 | 9/2001 |
| EP | 1757324 A2 | 9/2001 |
| JP | 04-027374 | 1/1992 |
| JP | 4145048 A | 5/1992 |
| JP | 06-038723 A | 2/1994 |
| JP | 7135938 A | 5/1995 |
| JP | 8023939 A | 1/1996 |
| JP | 09-266767 | 10/1997 |
| JP | 10183164 A | 7/1998 |
| JP | 10248501 A | 9/1998 |
| JP | 2000-308477 | 11/2000 |
| JP | 2001136931 A | 5/2001 |
| JP | 2002080355 A | 3/2002 |

OTHER PUBLICATIONS

English Language Abstract for JP10183164 taken from esp@cenet.com.
English Language Abstract for JP4145048 taken from esp@cenet.com.
English Language Abstract for JP 6038723.
English Language Abstract for JP 7135938.
English Language Abstract for JP 8023939.
English Language Abstract for JP 10248501.
English Language Abstract for JP 2002080355.
Trugo et al., Chlorogenic Acid Composition of Instant Coffees, Analyst, Mar. 1984, vol. 109, pp. 263-266.
International Search Report for PCT/CH02/00315 dated Oct. 29, 2002.
Patent Abstracts of Japan—Abstract for JP 2000-308477.
Patent Abstracts of Japan—Abstract for JP 09-266767.
Patent Abstracts of Japan—Abstract for JP 06-038723.
Patent Abstracts of Japan—Abstract for JP 04-027374.
PCT International Search Report for PCT/CH02/00282 dated Oct. 29, 2002.
Hernandez et al, "Variations in the Phenolic Composition of Fruit Juices with Different Treatments", European Food Research and Technology, Springer, Heidelberg, DE, vol. 204, No. 2, 1997, pp. 151-155, XP001041457, ISSN: 1431-4630.
J.J.L.Cilliers, et al., "Total Polyphenols in Apples and Ciders; Correlation with Chlorogenic Acid", Journal of Food Science, vol. 55, No. 5, 1990, pp. 1458-1459.
T. Ueki, et al., "Determination of Chlorogenic Acids and Caffeine in Coffee Containing Beverages via High Performance Liquid Chromatograph", pp. 40-49.

*Primary Examiner* — Leslie A Wong
(74) *Attorney, Agent, or Firm* — Curatolo Sidoti Co., LPA; Salvatore A. Sidoti; Floyd Trillis, III

(57) ABSTRACT

A consumable comprising an ingredient or ingredients that cause an off-taste in the consumable, and a chlorogenic acid provided in a concentration sufficient to mask or modify the off-taste. The chlorogenic acid may be supplied as an extract from a botanical source obtained by extraction at 30-80° C. with water and/or a polar organic solvent. The method of making an off-taste by addition of a chlorogenic acid to a consumable is also claimed.

22 Claims, No Drawings

TASTE MODIFIERS COMPRISING A CHLOROGENIC ACID

This is a Continuation patent application based on U.S. Ser. No. 13/436,254 filed Mar. 30, 2012, now abandoned, which in turn is a Divisional patent application of U.S. Ser. No. 10/480,372 filed Jun. 3, 2004, now U.S. Pat. No. 8,197,875, which in turn was filed as an application filed under 35 USC 371 of PCT/CH2002/000315, filed Jun. 12, 2002, which application claims the priority benefit of US Ser. No. 09/880,420 filed Jun. 13, 2001, now abandoned. The entire contents of the foregoing applications are herein incorporated by reference into the present specification. The applicant also claims all available priority benefit to the foregoing applications.

The invention relates to consumables, the taste profiles of which may be modified by the addition of chlorogenic acid.

Various consumables, such as food products, beverages and pharmaceuticals, contain substances that may provide or cause bitter notes and adversely affect the overall flavor of the product. In many instances, the flavor quality of such consumables would be improved by diminishing or removing the bitter notes, while at the same time preserving or enhancing the contribution made to the overall flavor by the non-bitter flavor components.

Non-nutritive sweeteners, also called artificial sweeteners, for example saccharine and aspartame, are only one example of substances that provide bitter notes. Therefore consumables such as beer, coffee, soft drinks, desserts and pharmaceutical products that are sweetened with non-nutritive sweeteners may possess bitter flavors or after-flavors that are generally regarded as undesirable by many consumers.

Because of the prevalence and popularity of non-nutritive sweeteners in consumables, several processes have been described for modifying the taste profile of consumables that contain these non-nutritive sweeteners. For example, U.S. Pat. No. 3,296,079 discloses the addition of 0.003% to 160% maltol to edible foodstuffs sweetened with non-nutritive sweetening agents to mask unpleasant aftertastes. U.S. Pat. No. 4,304,794 discloses the addition of aliphatic polyols to minimize the bitter aftertaste of 2,4,6,3'-tetrahydroxy-4'-methoxydihydrochalcone. U.S. Pat. Nos. 4,758,438; 3,647,482; and 3,667,969 disclose that the bitter aftertaste of saccharine is diminished by addition of the proteins thaumatin and monellin, by addition of ribonucleosides, ribonucleotides and their deoxy analogs, and by addition of D-galactose, respectively. U.S. Pat. No. 5,336,513 discloses that certain derivatives of cinnamic acid and their salts inhibited the bitterness of consumable materials, such as pharmaceutical preparations, foodstuffs and beverages that were sweetened with the artificial sweeteners saccharine and acesulfame K.

Processes have also been described for modifying a foodstuff or beverage by enhancing its sweetness characteristics. For example, U.S. Pat. Nos. 3,867,557 and 3,908,026 disclose that mixing or co-dissolving para-methoxycinnamaldehyde (PMCA) with other known natural or synthetic sweetening agents results in a composition having enhanced sweetness characteristics. These patents also disclose that PMCA enhances the flavor characteristics of vanillin and instant coffee, while suppressing their associated bitterness.

Processes disclosed in U.S. Pat. Nos. 3,924,017 and 3,916,028 show that salts of chlorogenic acid, caffeic acid, cynarine, and their isomers induce sweetness, and impart a very pleasant, sweet character to non-sweet foodstuffs or to foods with very low sweetness, such as water and milk.

The above-described activity in the prior art reflects the need for further and better methods and products for modifying unpleasant off-tastes often present in consumables.

Surprisingly, we have now found that unpleasant off-tastes in consumables may be modified or the taste or taste perception may be improved by the inclusion of chlorogenic acid in said consumables.

Therefore, the invention provides in a first aspect a consumable comprising an amount of chlorogenic acid sufficient to modify off-tastes of said consumables.

The amount of chlorogenic acid added to the consumable is sufficient to modify the off-taste, and may be used, for example at a concentration of about $0.0001\%^{w/v}$ to about $0.1\%^{w/v}$, more preferably of about $0.001\%^{w/v}$ to about $0.01\%^{w/v}$ in the consumable. However, the skilled person will appreciate that the off-taste reducing effect or the taste-enhancing effect will depend upon a number of factors, for example the type of consumable, the source of chlorogenic acid, the qualitative and/or quantitative modification desired, the substance(s) imparting an off-taste, and the presence of other desirable or undesirable taste components, and that it may be possible for a flavorist to achieve the desirable effects working inside or outside this range.

Off tastes may be formed as the result of one or more ingredients being added to, or present in, food products. An off-taste may be imparted by a non-nutritive (artificial) sweetener. Off-tastes produced by non-nutritive sweeteners have been described as being metallic and/or bitter. Non-nutritive sweeteners are present in vast categories of consumables including, but not limited to, soft drinks, dairy products, dessert products, savory products, salad dressings, sauces, condiments, alcoholic beverages, confections, gums, and medicaments. Examples of non-nutritive sweeteners include L-aspartyl-L-phenylalanine methyl ester (aspartame), saccharine and salts thereof, acesulfame salts (e.g., acesulfame K), cyclohexylsulfamic acid, dihydrochalcones, xylitol, neotame, sucralose, alitame cyclamates, steviol derivatives, and the like.

In another aspect of the invention, consumables contain an amount of chlorogenic acid sufficient to modify or mask the off-taste imparted by an artificial sweetener.

An off-taste may be imparted by alcohol in the consumable product. Alcohols include both grain alcohols and fermentation products (beer and wine), either alone or in combination with other components. Off-tastes produced by alcohols have been described as imparting a burning taste. The concentration of chlorogenic acid in a consumable containing alcohol may be in the range of about $0.0001\%^{w/v}$ to about $0.1\%^{w/v}$, more preferably of about $0.001\%^{w/v}$ to about $0.1\%^{w/v}$, most preferably of about $0.003\%^{w/v}$ to about $0.05\%^{w/v}$.

An off-taste may be imparted by a soy product. As used herein, soy includes all consumables containing soy in any form, including soybean oil used either alone, in combination, for example as a nutraceutical, or as a medicament, soy bean curd, soy milk, soy butter or soy paste. Off-tastes produced by soy products have been described as imparting a beany, aldehyde-like taste. In one aspect of the invention, the concentration of chlorogenic acid in a consumable containing a soy product may be in the range of about $0.0001\%^{w/v}$ to about $0.1\%^{w/v}$, more preferably about $0.0005\%^{w/v}$ to about $0.05\%^{w/v}$, most preferably about $0.001\%^{w/v}$ to about $0.01\%^{w/v}$.

An off-taste may be due to carbonation in the product. Examples of carbonated products include colas, citrus-flavored beverages, ales, beers and other consumables containing these products such as ices and frozen confections.

Off-tastes produced by carbonated products have been described as imparting a burning sensation. The concentration of chlorogenic acid in a carbonated product may be in the range of about $0.0001\%^{w/v}$ to about $0.1\%^{w/v}$, more preferably about $0.0005\%^{w/v}$ to about $0.05\%^{w/v}$, most preferably about $0.001\%^{w/v}$ to about $0.02\%^{w/v}$.

Besides modifying an off-taste, chlorogenic acid may also mask an off-taste by reducing its perception and/or enhance an overall sweetness perception.

As used herein, the term "consumable" broadly includes all products for use by human or animal that are ingested or products which may be placed in the mouth and subsequently discarded by the user. These encompass foods and beverages whether or not they provide nutritive value in all forms, e.g. cereal products, rice products, tapioca products, sago products, baker's products, biscuit products, pastry products, bread products, confectionery products, desert products, gums, chewing gums, chocolates, ices, honey products, treacle products, yeast products, baking-powder, salt and spice products, savory products, mustard products, vinegar products, sauces (condiments), tobacco products, cigars, cigarettes, processed foods, cooked fruit and vegetable products, meat and meat products, jellies, jams, fruit sauces, egg products, milk and dairy products, cheese products, butter and butter substitute products, milk substitute products, soy products, edible oils and fat products, medicaments, beverages, alcoholic drinks, beers, soft drinks, mineral and aerated waters and other non-alcoholic drinks, fruit drinks, fruit juices, coffee, artificial coffee, tea, cocoa, including forms requiring reconstitution, food extracts, plant extracts, meat extracts, condiments, sweeteners, nutraceuticals, gelatins, pharmaceutical and non-pharmaceutical gums, tablets, lozenges, drops, emulsions, elixirs, syrups and other preparations for making beverages.

Chlorogenic acid may be added directly to a consumable, or it may be pre-mixed with certain ingredients of the consumable. For example, it may be admixed with ingredients responsible for the creation of an off-taste to form a composition that may be thereafter added to the remaining ingredients of the consumable.

In another aspect of the present invention, there is provided a composition for addition to a consumable or ingredient of a consumable which composition contains ingredients responsible for creating an off-taste, and chlorogenic acid. The skilled person would appreciate that the precise amount of chlorogenic acid in said composition, for example in a sweetening composition, would vary within wide limits, provided that the composition is admixed to a consumable in an amount sufficient to provide an off-taste masking or taste enhancing effect. In particular the composition may contain sufficient chlorogenic acid in order that when admixed to a consumable the concentration in the consumable is about $0.0001\%^{w/v}$ to about $0.1\%^{w/v}$.

In a preferred embodiment, there is provided a sweetening composition comprising a non-nutritive sweetener and chlorogenic acid.

In yet another aspect of the present invention there is provided a method of providing chlorogenic acid to a consumable, comprising the step of adding chlorogenic acid, e.g. in form of a solution, to a consumable in an amount sufficient to modify or mask off-tastes and/or modify or enhance taste. Preferably, chlorogenic acid is added in an amount of about $0.0001\%^{w/v}$ to about $0.1\%^{w/v}$ to the consumable.

In one embodiment the method comprises admixing chlorogenic acid with ingredients responsible for imparting an off-taste to form a composition, which may be added to a consumable or to an ingredient of a consumable.

The invention provides in another of its aspects a method of providing chlorogenic acid to a consumable.

In a method of the present invention, a solution of chlorogenic acid may be added to the consumable to modify or mask an off-taste imparted by one or more substances, such as an artificial sweetener. Alternatively, chlorogenic acid may be added to the ingredients responsible for the off-taste to form a composition, which is thereafter added to the consumable. The total concentration of chlorogenic acid in the consumable ranges from about $0.0001\%^{w/v}$ to about $0.1\%^{w/v}$.

Chlorogenic acid is a trivial name used somewhat loosely in the literature to describe a range of phenolic acids found in plant materials. For example, in some literature references, 5-caffeoylquinic acid alone is referred to as "chlorogenic acid". As used herein, however, the term chlorogenic acid is used to describe one or more of a family of esters that form between certain cis or trans cinnamic acids and quinic acid.

The family of esters are set forth in Clifford, *J. Sci. Food Agric.*, 2000, 80, pp. 1033-1043, which is expressly incorporated by reference herein in its entirety, Clifford subdivides chlorogenic acid by the identity, number, and position of the acyl residues on the quinic acid. This reference teaches that the most common individual chlorogenic acid is 5-O-caffeoylquinic acid (5-CQA), whose structure is shown below, and that while 5-CQA is commonly referred to as chlorogenic acid (CGA), this is a term which should be used only to refer to the family of related quinic acid conjugates.

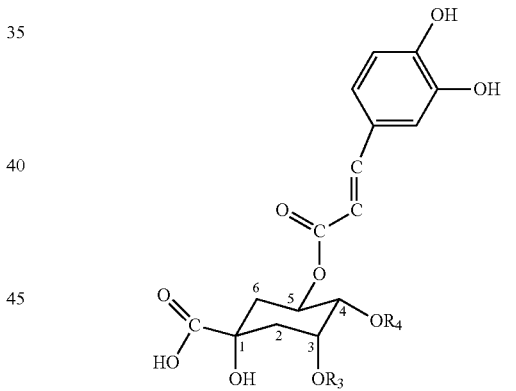

The structure of quinic acid (1R-(1α, 3α, 4α, 5β)-1, 3, 4, 5 tetrahydroxy-cyclohexane carboxylic acid) is shown below.

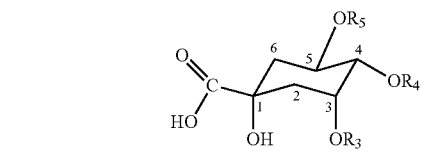

Quinic Acid: $R_3 = R_4 = R_5 = H$

Quinic acid has axial hydroxyl groups (on carbons 1 and 3) and equatorial hydroxyl groups (on carbons 4 and 5). Substitutions on the R groups produce various types of chlorogenic acid, as derived from Clifford, *ASIC*, 17 colloque, Nairobi, 1997, pp. 79-91, which is expressly incorporated by reference herein in its entirety and listed in Table 1, where CQA is caffeoylquinic acid, FQA is feruloylquinic acid, CoQA is coumaroylquinic acid, and CFQA is caffeoylferuloylquinic acid.

TABLE 1

| Compound | Identity of R3 | Identity of R4 | Identity of R5 |
| --- | --- | --- | --- |
| 3-CQA | caffeic acid | H | H |
| 4-CQA | H | caffeic acid | H |
| 5-CQA | H | H | caffeic acid |
| 3-FQA | ferulic acid | H | H |
| 4-FQA | H | ferulic acid | H |
| 5-FQA | H | H | ferulic acid |
| 3-p-CoQA | p-coumaric acid | H | H |
| 4-p-CoQA | H | p-coumaric acid | H |
| 5-p-CoQA | H | H | p-coumaric acid |
| 3,4-diCQA | caffeic acid | caffeic acid | H |
| 3,5-diCQA | caffeic acid | H | caffeic acid |
| 4,5-diCQA | H | caffeic acid | caffeic acid |
| 3,4-CFQA | caffeic acid | ferulic acid | H |
| 3,4-CFQA | ferulic acid | caffeic acid | H |
| 3,5-CFQA | caffeic acid | H | ferulic acid |
| 3,5-CFQA | ferulic acid | H | caffeic acid |
| 4,5-CFQA | H | caffeic acid | ferulic acid |
| 4,5-CFQA | H | ferulic acid | caffeic acid |

Both cis- and trans-configurations of the cinnamic acids are known to exist in nature, although the cinnamic acids in chlorogenic acid are predominantly in the trans-configuration. The structures of various acids or derivatives belonging to the cinnamic acid family are shown below in the trans-configuration.

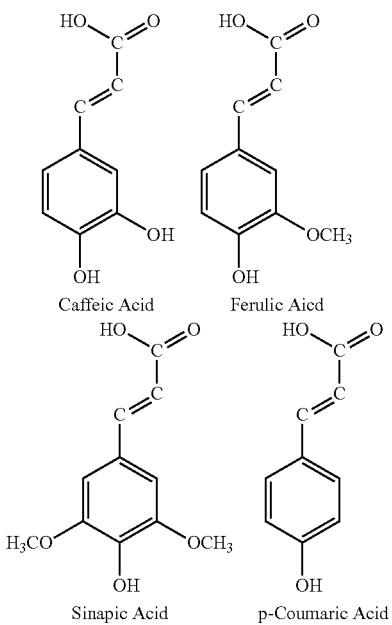

Cinnamic acids and their derivatives, used as sweetness enhancers/inducers in various products, encompass a series of 3-phenyl-propenoic acids that differ in the chemical groups substituted on the aromatic ring. They are widely distributed as organic conjugates in a variety of plant materials, and are rarely found as free acids in unprocessed plant material. Besides cinnamic acid itself, the most common of the cinnamic acids in this family are caffeic acid (3,4-dihydroxycinnamic acid), ferulic acid (3-methoxy-4-hydroxycinnamic acid), sinapic acid (3,5-dimethoxy-4-hydroxycinnamic acid), and p-coumaric acid (p-hydroxycinnamic acid).

Chlorogenic acid is widely distributed in the plant kingdom and occurs in fruits, leaves and other tissues of dicotyledonous plants. It may be extracted from a variety of natural sources such as green coffee beans (e.g., arabica, robusta and liberica), leaves of *Ilex paraguariensis*, pome fruits (e.g., apples and pears), stone fruits (e.g., cherries and plums), berry fruits, citrus fruits, brassica vegetables (e.g., kale, cabbage and brussel sprouts), solanaceae (e.g., potato tubers, tomatoes, and aubergines), asteraceae (e.g., chicoryroot and artichokes), and a variety of other miscellaneous vegetables. It may also be found in cereal grains (e.g., oats, barley, rye, rice, corn and wheat). The amount and different types of chlorogenic acid that are present vary depending upon the source. Chlorogenic acid may be extracted from one or more botanical sources, and/or synthetic chlorogenic acid may be used.

Green coffee beans are a good source of chlorogenic acid (Clifford, *ASIC,* 17 colloque, Nairobi, 1997 pp. 79-91). Specifically, green coffee bean extracts contain the following types of chlorogenic acid: three mono-esters of caffeic and quinic acid, namely, 3-caffeoylquinic acid (3-CQA), 4-caffeoylquinic acid (4-CQA), and 5-caffeoylquinic acid (5-CQA); three mono-esters of p-coumaric and quinic acid: p-coumaroylquinic acids (3-p-CoQA, 4-p-CoQa, 5-p-CoQA); three mono-esters of ferulic and quinic acid: feruloylquinic acids (3-FQA, 4-FQA, 5-FQA); and three di-esters of caffeic and quinic acid: namely, 3,4-dicaffeoylquinic acid (3,4-di CQA), 3,5-dicaffeoylquinic acid (3,5-di CQA), and 4,5-dicaffeoylquinic acid (4,5-di CQA). In addition, there are also six mixed di-esters of caffeic, ferulic, and quinic acid known as the caffeoylferuloylquinic acids (two 3,4-CFQA, two 3,5-CFQA, two 4,5 CFQA).

The amounts of several of these types of chlorogenic acid found in extracts of green Robusta coffee beans have been reported. These values, as follows, are expressed as g/kg of dry green coffee beans: 7.32 g 3-CQA, 11.25 g 4-CQA, 49.66 g 5-CQA, 6.04 g 5-FQA, 5.05 g 3,4-di CQA, 4.61 g 3,5-di CQA, and 4.11 g 4,5-di CQA (Trugo and Macrae, *Food Chemistry,* 1984, 15, pp. 219-227, which is expressly incorporated by reference herein in its entirety). While the presence of chlorogenic acid in green coffee bean extracts is known, the use of chlorogenic acid to decrease off-taste in various types of consumables has not previously been reported.

Accordingly, the invention provides in another aspect a consumable containing an amount sufficient for taste modification or taste enhancement of chlorogenic acid derived from green coffee bean extract. A particular source of chlorogenic acid are green robusta coffee beans. In the following paragraphs there is disclosed methodology for extracting chlorogenic acid from robusta beans. However, the skilled person will appreciate that the procedure may be modified to extract chlorogenic acid from other plant sources.

Green robusta coffee beans may be extracted with constant agitation in solvents composed of water and polar organic solvents. The organic solvents that may be used include methanol, ethanol, n-propanol, 2-propanol, acetone and propylene glycol. The beans may either be the regular beans or decaffeinated beans. They may be extracted either as whole beans or after grinding. The extraction may be carried out either with water alone or with water in combination with one or more solvents listed above. The preferred solvents are methanol and ethanol. The composition of the solvents may range between 100/0 water/organic solvent (w/w) to 10/90 water/organic solvent (w/w). The extraction temperature may be between 30° C. to 80° C. and the extraction time may be between 4 hours and 40 hours. The preferred temperature is between 45° C. to 60° C. for maximal extraction efficiency without causing significant isomerization of 5-CQA. Extraction may be carried out with equipment known to those skilled in the art, such as a counter current extractor or an extractor with constant solvent circulation. It will be obvious to those skilled in the art that the extraction can be carried out in various types of equipment.

The extract may be collected either by decanting, centrifuging or filtering. The beans optionally may then be extracted one or two more times under similar conditions, and the extracts combined and the solvents evaporated under vacuum to concentrate the extract to about 1 to 3 times of the bean weight. The concentrated extract may be further cleaned up to a higher chlorogenic acid content by one of the following methods.

An organic solvent that is miscible with water may be added to the concentrated extract to induce precipitation of proteins and other materials that are insoluble in those organic solvents. Preferably the solvent used is ethanol, but other solvents including methanol, acetone, n-propanol or 2-isopropanol may also be used. The amount of the organic solvent needed for protein precipitation may range from 1 to 4 times the extract weight depending on the amount of chlorogenic acid desired. After about 1 hour, protein precipitation is complete and the protein removed by, e.g. centrifugation or filtration.

Alternatively, the concentrated extract may be washed by an organic solvent or solvents, which are not miscible with water. The solvents that may be used include hexane, cyclohexane, heptane, dichloromethane, chloroform, toluene, petroleum ether, methyl t-butyl ether, ethyl acetate and butanol. The amount of solvent used may vary from one half times of the extract weight to four times of the extract weight. To facilitate the phase separation, a second solvent that is miscible with water may be added. The amount of the second solvent added may be up to 20% of the extract weight. The second solvent that may be used includes methanol, ethanol, acetone, n-propanol and 2-propanol. Normally, one washing step is sufficient to clarify the extract. However, additional washing may be performed if necessary. After the phase separation is reached the aqueous phase may be collected and treated under vacuum to have the residual solvents removed.

Still alternatively, the concentrated extract may be passed through a microfiltration cartridge to remove the impurities. The cut-off molecular weight of the cartridge used for this operation may be as low as 10,000 Da. The extract may be filtered at first through a filter of a large pore size to remove the large particles in the extract followed by filter of a smaller pore size to remove the smaller particles in the extract. The same procedure may be repeated with filters of different pore size until a clear permeate is obtained. The materials retained by the cartridge may be discarded and the materials that permeate the filter may be collected for further processing.

Still alternatively, the concentrated extracted may be cleaned by passing through an adsorption column. The adsorption may be achieved with any types of the commercial resins that operate based on the principle of the hydrophobic affinity between the molecules and the resins. The extract may be passed through a column containing such resin or resins. The pass-through may be discarded and chlorogenic acid may be recovered by eluting the column with water containing a water mixable organic solvent. The organic solvents that may be used to elute the column include methanol, ethanol, acetone, n-propanol and 2-propanol. The ratio of water to the organic solvent may vary from 90/10 to 0/100 water/organic solvent (w/w). The total amount of solvent used to elute the column is at least one times of the bed volume of the column, but may be increased to 5 times of the bed volume of the column for a more complete recovery of chlorogenic acid. The material collected from the column may be treated under vacuum to have the organic solvents removed.

The aqueous solution obtained after any of the above operations may be further concentrated under vacuum. It may be directly dried under vacuum to a tan-colored powder. Alternatively, it may be concentrated to a solid content of about 20% to 45% of the total weight, followed by spray-drying to a tan-colored powder. The spray-drying may be performed with or without carriers.

EXAMPLE 1

Extraction and Purification by Precipitation

Whole green robusta coffee beans (21.8 kg) are extracted with a water and ethanol (95%) mixture at a ratio of 85/15 w/w. The beans are loaded in a conical-shaped extractor and the solvent is circulated at 60° C. for 16 hours. The extract is collected by draining from the extractor and the residual beans are extracted with fresh solvent of the same composition for two more times. The amount of solvent used for each extraction is between 2 to 4.5 times of the bean weight. The extracts are combined and concentrated to 36.3 kg. An amount of ethanol equal to the extract weight is added to induce the precipitation of protein and other insoluble material in the extract. The precipitation is discarded and the supernatant is collected by filtration and further concentrated to 9.8 kg. The concentrated extract is spray-dried without addition of carrier to form a tan-colored powder. For every kilogram of green coffee bean, 146 gram of powder is obtained. The powder is water-soluble, it forms a clear solution in water. The chlorogenic acid content is analyzed by HPLC. The analysis reveals the presence of several different types of chlorogenic acid, which amount to about 35% of the total mass of the extract. The proportions of the various types of chlorogenic acid separated by HPLC and quantitated as a weight per weight percentage are shown in the table below.

| 3-CQA (% w/w) | 4-CQA (% w/w) | 5-CQA (%w/w) | FQAs (% w/w) | di-CQAs (% w/w) | FCQAs (% w/w) | Total Chlorogenic acid |
|---|---|---|---|---|---|---|
| 5.71 | 5.63 | 11.52 | 5.07 | 5.92 | 1.24 | 35.09 |

EXAMPLE 2

Extraction and Purification by Washing (Phase Separation)

Whole green Robusta coffee beans (22.7 kg) are extracted with a water and ethanol (95%) mixture at ratio of 40/60 w/w. The beans are loaded in a conical-shaped extractor and the solvent is circulated at 60 C for 16 hours. The extract is collected by draining from the extractor and the residual beans are extracted with fresh solvent of the same composition for two more times. The amount of solvent used for each extraction is between 2 to 4.5 times of the bean weight. The extracts are combined and partially concentrated to 64.9 kg. The extract is washed with an equal weight of ethyl acetate/ethanol mixture (85/15 w/w) once. The ethyl acetate layer is collected and subsequently discarded. The aqueous layer is collected and dried under vacuum to a tan-colored powder. For every kilogram of green coffee bean, 178 gram of powder is obtained. The powder is water-soluble; it forms a clear solution in water. The chlorogenic acid was analyzed by HPLC and the results are summarized as follows.

| 3-CQA (% w/w) | 4-CQA (% w/w) | 5-CQA (%w/w) | FQAs (% w/w) | di-CQAs (% w/w) | FCQAs (% w/w) | Total Chlorogenic acid |
|---|---|---|---|---|---|---|
| 2.40 | 3.57 | 20.17 | 5.62 | 7.69 | 1.43 | 40.88 |

EXAMPLE 3

Extraction and Purification by Microfiltration

Whole green Robusta coffee beans (22.7 kg) are extracted with a water and ethanol (95%) mixture at ratio of 40/60 w/w. The beans are loaded in a conical-shaped extractor and the solvent is circulated at 60 C for 16 hours. The extract is collected by draining from the extractor and the residual beans are extracted with fresh solvent of the same composition for two more times. The amount of solvent used for each extraction is between 2 to 4.5 times of the bean weight. The extracts are combined and partially concentrated to 64.9 kg. An aliquot of 6.8 kg of the extract is passed through a microfilter with a molecular cut-off value at 10,000 Da. The materials retained by the filter are discarded and the materials that permeate through the filter are concentrated and dried. For every kilogram of green coffee bean, 146 grams of a tan-colored powder are obtained. The powder is water-soluble; it forms a clear solution in water. The chlorogenic acid is analyzed by HPLC and the results are summarized as follows.

| 3-CQA (% w/w) | 4-CQA (% w/w) | 5-CQA (%w/w) | FQAs (% w/w) | di-CQAs (% w/w) | FCQAs (% w/w) | Total Chlorogenic acid |
|---|---|---|---|---|---|---|
| 2.22 | 3.81 | 22.33 | 5.84 | 8.53 | 1.56 | 44.30 |

EXAMPLE 4

Extraction and Purification by Chromatography (Adsorption Resin)

Whole green Robusta coffee beans (66.7 kg) are loaded in a conical-shaped extractor and water is circulated at 80° C. for 16 hours. The extract is collected by draining from the extractor and the residual beans are extracted with water for two more times. The amount of water used for each extraction is between 2 to 4.5 times of the bean weight. The extracts are combined and concentrated to 102.1 kg. An aliquot of 200 g of the extract is further concentrated to 120 g and loaded on a column filled with Amberlite XAD-4 adsorption resin (wet mesh size 20-60). The column is 4 cm in diameter and 38 cm long with a column bed volume of 427 ml. The column is eluted with 6 bed volumes of water followed by 4.3 bed volumes of ethanol/water (50/50 w/w). The last 2 bed volumes of the ethanol/water (50/50 w/w) elution are collected and dried to a light tan-colored powder. For every kilogram of green coffee bean, 62 grams of powder are obtained. The powder is water-soluble; it forms a clear solution in water. The chlorogenic acid was analyzed by HPLC and the results are summarized as follows.

| 3-CQA (% w/w) | 4-CQA (% w/w) | 5-CQA (% w/w) | FQAs (% w/w) | di-CQAs (% w/w) | FCQAs (% w/w) | Total Chlorogenic acid |
|---|---|---|---|---|---|---|
| 4.90 | 11.39 | 21.17 | 9.48 | 11.27 | 0.67 | 58.88 |

EXAMPLE 5

Extraction and Removal of Precipitate by Centrifugation/Filtration

About 4.0 kg of green Robusta coffee beans are mixed with constant agitation in 16.0 kg of water at 80° C. for at least four hours. The extract is collected either by decanting, centrifuging, or filtering. The beans are then extracted with an additional 6 kg of water at 80° C. for at least another four hours. The extracts are combined and the water is evaporated by vacuum to concentrate the extract to about 5 or 6 kg. An amount of ethanol (95%) equal to one and one-half times the weight of the concentrated extract is added; the amount of ethanol may be increased to about four times the weight of the concentrated extract if a higher content of chlorogenic acid in the final extract is desired. The mixture is stirred for 15 minutes, and the slurry is allowed to stand at ambient temperature for at least one hour. The resulting precipitate is removed by either centrifugation or filtration and is subsequently discarded. The ethanol is evaporated from the supernatant or filtrate under vacuum, and the aqueous solution is dried under vacuum to yield about 460-500 g of a tan-colored powder. Alternatively, the aqueous solution may be concentrated to an appropriate solid content of about 30% to 45% of the total weight, followed by spray-drying the concentrated aqueous solution to a tan colored powder. The powdered extract is soluble in water. It forms a clear solution in water. The chlorogenic acid is analyzed by HPLC and the results are summarized as follows.

| 3-CQA (% w/w) | 4-CQA (% w/w) | 5-CQA (% w/w) | FQAs (% w/w) | di-CQAs (% w/w) | FCQAs (% w/w) | Total Chlorogenic acid |
|---|---|---|---|---|---|---|
| 8.6 | 8.4 | 16.7 | 8.9 | 5.8 | 3.0 | 51.4 |

In all the examples, the extract is analyzed by high performance liquid chromatography (HPLC) using a Prodigy ODS-3 column (150×4.6 mm, particle size 5 μm) (Phenomenex, Torrance, Calif.) at ambient temperature, interfaced with a mass spectroscopic detector (MSD) to measure chlorogenic acid. The gradient used for elution of the compounds is given in Table 2.

TABLE 2

| Time (min) | Flow Rate (ml/min) | Acetonitrile/0.1% Trifluoroacetic acid | Water/0.1% Trifluoroacetic acid |
|---|---|---|---|
| 0  | 0.8 | 10 | 90 |
| 18 | 0.8 | 10 | 90 |
| 30 | 0.8 | 70 | 30 |
| 32 | 0.8 | 70 | 30 |
| 33 | 0.8 | 10 | 90 |
| 43 | 0.8 | 10 | 90 |

The conditions for MSD are as follows: atmospheric pressure chemical ionization mode, positive and negative polarity, gas temperature of 350° C., vaporizer temperature of 450° C., drying gas flow rate of 6.0 l/min nitrogen, nebulizer pressure of 35 psig, capillary voltage of 2500 V, corona current of 7 µA, and fragmentor voltage of 80 V. A standard curve is prepared using chlorogenic acid with the molecular formula of $C_{16}H_{18}O_9$ (catalog No. C44206, Aldrich, Milwaukee, Wis.).

Other types of chlorogenic acid are also likely present but are not detected using the conditions for analysis. It will be appreciated that the HPLC and MSD conditions may be modified to resolve different types of chlorogenic acid, and that the yield and content of chlorogenic acid may vary with different batches and different types of green coffee beans or different sources.

Extracts of chlorogenic acid from several batches of green coffee beans are prepared as solutions ranging from 2.8% $^{w/w}$ to 10% $^{w/w}$, pH ranging from about pH 4.5 to about pH 6.0, and are added to various consumables based on the weight of the powder. These solutions are added to consumables to modify and/or mask off-tastes.

EXAMPLE 6

Chlorogenic Acid (Synthetic) Added to an Aged Artificially Sweetened Beverage

An artificially sweetened beverage is prepared by mixing 1.4 g aspartame, 0.9 g acesulfame K, 6 ml sodium benzoate (25% $^{w/v}$ in water), 1.3 ml phosphoric acid (85% $^{w/v}$), and 0.5 ml citric acid (50% $^{w/v}$ in water). The volume of the mixture is adjusted to 1000 ml with water. The beverage mixture is aged for three weeks at 34° C.

A 2.8% $^{w/w}$ solution of a commercially available synthetic chlorogenic acid (>95% pure (1,3,4,5-tetrahydroxy-cyclohexanecarboxylic acid 3-[3,4-dihydroxycinnamate]), Sigma Chemical Co., St. Louis, Mo.), in water, pH 5.6, is added to a portion of the aged beverage to a final concentration of 0.003% $^{w/v}$. The beverage containing chlorogenic acid is evaluated and compared to the untreated beverage by a six member panel of trained flavorists. The beverage containing the commercial chlorogenic acid is judged by the panel to display markedly less of the metallic, slightly bitter aftertaste found in the aged artificially sweetened beverage.

EXAMPLE 7

Chlorogenic Acid (Extracted) Added to an Aged Artificially Sweetened Beverage

To another portion of the artificially sweetened beverage prepared as described in the first paragraph of Example 6, an aqueous solution of chlorogenic acid from the powdered extract of green coffee beans is added to a final concentration of 0.003% $^{w/v}$ chlorogenic acid. This beverage is evaluated by the same flavorist panel as described in Example 6. The beverage containing chlorogenic acid extracted from green coffee beans is also judged to display markedly less of the metallic, slightly bitter aftertaste found in the aged artificially sweetened beverage.

EXAMPLE 8

Chlorogenic Acid Added to an Unflavored Alcoholic Beverage

A 10 proof (5% alcohol) unflavored beverage is prepared by mixing 5.26 ml Grain Neutral Spirits (95% alcohol), 92.24 ml water, 2.0 ml high fructose corn syrup, 0.25 ml sodium benzoate (10% $^{w/v}$ in water), and 0.25 ml potassium sorbate (10% $^{w/v}$ in water).

A solution of chlorogenic acid from a green coffee bean extract, prepared as previously described, is added to a portion of the alcoholic beverage to a final concentration of 0.0035% $^{w/v}$ chlorogenic acid. The beverage containing chlorogenic acid is evaluated by a six member panel of trained flavorists. The beverage is judged to display significantly less of the alcohol-burn taste than that observed in the untreated beverage.

EXAMPLE 9

Chlorogenic acid Added to a Soy Product

A solution of chlorogenic acid from a green coffee bean extract, prepared as previously described, is added to a commercial soy milk product (White Wave, Silk Chocolate) to final concentration of 0.04% $^{w/v}$ chlorogenic acid.

A six member panel of trained flavorists evaluating the product containing chlorogenic acid find the soy milk's beany aldehydic soy off-notes to be masked and perceive the product to be smoother and creamier in comparison to the product without chlorogenic acid.

EXAMPLE 10

Chlorogenic Acid Added to a Flavored Carbonated Beverage

A solution of chlorogenic acid from a green coffee bean extract, prepared as previously described, is added to a standard carbonated orange flavored beverage (flavor level 0.2%) to final concentration of 0.001% $^{w/v}$ chlorogenic acid.

A six member panel of trained flavorists compared the carbonated beverages with and without addition of chlorogenic acid. The panel finds the beverage containing chlorogenic acid to have a significantly lowered impact of the sharp, slightly burning sensation of the carbonation when compared to the beverage without added chlorogenic acid.

EXAMPLE 11

Chlorogenic Acid Added to Aspartame Sweetened Yogurt

A solution of chlorogenic acid from a green coffee bean extract, prepared as previously described, is added to a commercial non-fat yogurt (Dannon, Light 'n Fit Vanilla Yogurt, with Aspartame & fructose added) to a final concentration of 0.005% $^{w/v}$ chlorogenic acid.

A panel of six trained flavorists compares the yogurts with and without addition of chlorogenic acid. The panel judges that the product containing chlorogenic acid displays an improved body and texture in the mouth, and that the overall sweetness perception is fuller and more rounded than the yogurt without addition of chlorogenic acid.

The invention claimed is:

1. A consumable comprising a an ingredient or ingredients that provide or cause an off-taste to the consumable, and an off-taste masking and/or modifying agent comprising a chlorogenic acid, wherein the chlorogenic acid is present in the consumable in a concentration of 0.0001%$^{w/v}$ to 0.1%$^{w/v}$.

2. The consumable according to claim 1, wherein the off-taste is a bitter aftertaste or is a metallic off-taste.

3. The consumable according to claim 1, wherein the chlorogenic acid is derived from green coffee bean extract.

4. The consumable according to claim 3, wherein the chlorogenic acid is derived from an extract of green robusta coffee beans.

5. The consumable of claim 1, wherein the consumable is selected from the group consisting of: cereal products, rice products, tapioca products, sago products, baker's products, biscuit products, pastry products, bread products, confectionery products, desert products, gums, chewing gums, chocolates, ices, honey products, treacle products, yeast products, baking-powder, salt and spice products, savory products, mustard products, vinegar products, sauces (condiments), tobacco products, cigars, cigarettes, processed foods, cooked fruits and vegetable products, meat and meat products, jellies, jams, fruit sauces, egg products, milk and dairy products, cheese products, butter and butter substitute products, milk substitute products, edible oils and fat products, medicaments, beverages, alcoholic drinks, beers, soft drinks, mineral and aerated waters and other non-alcoholic drinks, fruit drinks, fruit juices, coffee, artificial coffee, tea, cocoa, including forms requiring reconstitution, food extracts, plant extracts, meat extracts, condiments, sweeteners, nutraceuticals, gelatins, pharmaceutical and non-pharmaceutical gums, tablets, lozenges, drops, emulsions, elixirs, syrups and other preparations for making beverages, and combinations thereof.

6. The consumable according to claim 1 containing chlorogenic acid at a concentration of about 0.001%$^{w/v}$ to about 0.1%$^{w/v}$.

7. The consumable according to claim 1, wherein the consumable is carbonated, and in which the concentration of chlorogenic acid is about 0.0005%$^{w/v}$ to about 0.05%$^{w/v}$.

8. The consumable according to claim 1 wherein the chlorogenic acid is selected from the group consisting of 3-CQA, 4-CQA, 5-CQA, 3-FQA, 4-FQA, 5-FQA, 3-p-CoQA, 4-p-CoQA, 5-p-CoQA, 3,4-diCQA, 3,5-diCQA, 4,5-diCQA, 3,4-CFQA, 3,5-CFQA, 4,5-CFQA, and combinations thereof.

9. A consumable according to claim 8 wherein the chlorogenic acid comprises at least two of: 3-CQA, 4-CQA, 5-CQA, 3-FQA, 4-FQA, 5-FQA, 3-p-CoQA, 4-p-CoQA, 5-p-CoQA, 3,4-diCQA, 3,5-diCQA, 4,5-diCQA, 3,4-CFQA, 3,5-CFQA, or 4,5-CFQA.

10. A consumable according to claim 9 wherein the chlorogenic acid comprises at least three of: 3-CQA, 4-CQA, 5-CQA, 3-FQA, 4-FQA, 5-FQA, 3-p-CoQA, 4-p-CoQA, 5-p-CoQA, 3,4-diCQA, 3,5-diCQA, 4,5-diCQA, 3,4-CFQA, 3,5-CFQA, or 4,5-CFQA.

11. A taste-modifying composition comprising a chlorogenic acid which is effective in counteracting off-tastes imparted by an ingredient or ingredients present in a consumable, when the chlorogenic acid is present in a concentration of about 0.001%$^{w/v}$ to about 0.1%$^{w/v}$ in the consumable.

12. The consumable according to claim 11, wherein the off-taste is a bitter aftertaste or is a metallic off-taste.

13. The taste-modifying composition of claim 11, wherein the chlorogenic acid is derived from green coffee bean extract.

14. The taste-modifying composition of claim 13, wherein the chlorogenic acid is derived from an extract of green robusta coffee beans.

15. A taste-modifying composition of claim 13, wherein the chlorogenic acid is selected from the group consisting of: 3-CQA, 4-CQA, 5-CQA, 3-FQA, 4-FQA, 5-FQA, 3-p-CoQA, 4-p-CoQA, 5-p-CoQA, 3,4-diCQA, 3,5-diCQA, 4,5-diCQA, 3,4-CFQA, 3,5-CFQA, 4,5-CFQA, and combinations thereof.

16. A method for modifying the taste of a consumable comprising:

adding chlorogenic acid to the consumable in a concentration of about 0.001%$^{w/v}$ to about 0.1%$^{w/v}$ which amount modifies or masks a bitter aftertaste imparted by an ingredient or ingredients also present in the consumable.

17. The method of claim 16, wherein the off-taste is a bitter aftertaste or is a metallic off-taste.

18. The method of claim 16, wherein the consumable is derived from green coffee bean extract.

19. The method of claim 18, wherein the chlorogenic acid is derived from an extract of green robusta coffee beans.

20. A method according to claim 16, wherein the chlorogenic acid is selected from the group consisting of: 3-CQA, 4-CQA, 5-CQA, 3-FQA, 4-FQA, 5-FQA, 3-p-CoQA, 4-p-CoQA, 5-p-CoQA, 3,4-diCQA, 3,5-diCQA, 4,5-diCQA, 3,4-CFQA, 3,5-CFQA, 4,5-CFQA, and combinations thereof.

21. A method according to claim 20, wherein the chlorogenic acid comprises at least two of: 3-CQA, 4-CQA, 5-CQA, 3-FQA, 4-FQA, 5-FQA, 3-p-CoQA, 4-p-CoQA, 5-p-CoQA, 3,4-diCQA, 3,5-diCQA, 4,5-diCQA, 3,4-CFQA, 3,5-CFQA, or 4,5-CFQA.

22. A method according to claim 21, wherein the chlorogenic acid comprises at least three of: 3-CQA, 4-CQA, 5-CQA, 3-FQA, 4-FQA, 5-FQA, 3-p-CoQA, 4-p-CoQA, 5-p-CoQA, 3,4-diCQA, 3,5-diCQA, 4,5-diCQA, 3,4-CFQA, 3,5-CFQA, or 4,5-CFQA.

* * * * *